United States Patent [19]
Brannon

[11] Patent Number: 5,873,841
[45] Date of Patent: Feb. 23, 1999

[54] SYRINGE WITH DECELERATING DEVICE

[75] Inventor: James K. Brannon, Culver City, Calif.

[73] Assignee: Vascular Logics, Inc., Huntington Beach, Calif.

[21] Appl. No.: 797,091

[22] Filed: Feb. 7, 1997

[51] Int. Cl.$^6$ .................................................. A61B 5/00
[52] U.S. Cl. ............................................................ 600/578
[58] Field of Search ............................... 600/576, 577, 600/583; 604/187, 231, 239

[56] References Cited

U.S. PATENT DOCUMENTS

| | | | |
|---|---|---|---|
| 707,671 | 6/1902 | Billings | 604/218 |
| 1,272,742 | 7/1918 | Weguelin et al. | |
| 1,410,530 | 3/1922 | Larché | |
| 2,073,067 | 3/1937 | Klein et al. | 128/215 |
| 3,064,648 | 11/1962 | Bujan | 128/214 |
| 3,931,815 | 1/1976 | Takatsuki | 128/2 |
| 4,150,666 | 4/1979 | Brush | 128/2 |
| 4,274,408 | 6/1981 | Nomrod | 128/214.4 |
| 4,312,362 | 1/1982 | Kaufman | 128/763 |
| 4,378,812 | 4/1983 | Sarstedt | 128/765 |
| 4,412,832 | 11/1983 | Kling et al. | 604/164 |
| 4,660,569 | 4/1987 | Etherington | 128/765 |
| 4,813,938 | 3/1989 | Raulerson | 604/167 |
| 4,936,315 | 6/1990 | Lineback | 128/765 |
| 5,045,065 | 9/1991 | Raulerson | 604/167 |
| 5,133,362 | 7/1992 | Moss | 128/763 |
| 5,147,329 | 9/1992 | Brannon | 604/231 |
| 5,324,266 | 6/1994 | Ambrisco et al. | 604/125 |

FOREIGN PATENT DOCUMENTS

| | | |
|---|---|---|
| 20 25 800 A1 | 2/1982 | Germany . |
| WO 88/03778 | 6/1988 | WIPO . |

*Primary Examiner*—Max Hindenburg
*Attorney, Agent, or Firm*—Lyon & Lyon LLP

[57] ABSTRACT

A medical syringe for collecting blood samples is provided, comprising a cylindrical body having an open end and a closed end. A plunger assembly including a piston is slidably inserted into the open end, defining a fluid chamber between the piston face and the closed end. A distal opening in the closed end provides passage between the syringe and a patient, and includes a restriction therein. A conduit extends from the fluid chamber through the plunger assembly to a tube-holding device, or may extend peripherally from the cylindrical body to the tube-holding device. Fluid is drawn into the fluid chamber, and a vacuum specimen tube is inserted into the tube-holding device, the vacuum drawing fluid into the tube. The restriction in the distal opening imposes a viscous resistance to flow, slowing blood flow into the syringe, preferentially drawing fluid into the specimen tube from the fluid chamber, and decelerating movement of the plunger assembly. Alternatively a cannula extends between the distal opening and the conduit, the restriction substantially isolating a fluid sample in the fluid chamber from a sample drawn through the cannula.

21 Claims, 8 Drawing Sheets

SYRINGE WITH DECELERATING DEVICE

FIELD OF THE INVENTION

The present invention relates generally to medical syringes for withdrawing fluid from a patient, and more particularly to a syringe for collecting blood for laboratory testing having a decelerating device for slowing the proximal and distal movement of the plunger and consequently decelerating the influx and efflux of blood into the barrel of the syringe.

BACKGROUND

Many conventional devices are available for obtaining blood samples from a patient for laboratory testing. For example, a conventional syringe and a hypodermic needle are often used as is well known to those skilled in the art.

When multiple samples are needed for laboratory tests, traditionally, a blood collection needle is used. Generally, such devices include a pair of needles disposed in line axially on a central hub or housing. These needles are generally provided in a tube-holding device, typically a hollow cylindrical body with open ends. The hub of the blood collection needle is generally attached to one end such that one needle extends into the cylindrical body, while the other needle extends axially beyond the end of the cylindrical body for percutaneous introduction into a patient.

Conventional vacuum specimen tubes are then inserted into the other end of the cylindrical body. The rubber stopper of the specimen tube is punctured by the needle inside the cylindrical body, creating a continuous passage from the percutaneous needle tip to the specimen tube. Thus, after the blood collection needle has been introduced into a patient, a series of specimen tubes may be inserted into the cylinder to collect separate samples for testing.

One of the problems related to the use of such traditional devices is hemolysis. When the specimen tube is inserted into the blood collection device, the fixed vacuum of the tube draws blood through the passage quickly. The uncontrolled flow of blood caused by the force of this vacuum often causes red blood cells to shear and break down. Potassium is released from the cells into the blood fluid, creating inaccuracies in the laboratory tests performed on the samples.

Additionally, such conventional devices present problems in obtaining samples from patients having poor peripheral access, such as young and elderly patients whose veins are smaller or more susceptible to collapse.

Attempts have been made to modify these conventional blood collection devices to respond to these problems. For example, U.S. Pat. No. 5,133,362, by Moss, discloses a blood collection needle which uses a smaller gauge needle for introduction into the patient than is used for the specimen tubes. The device uses such smaller gauge needles to provide improved peripheral access, while also slowing blood flow through the needle to reduce hemolysis. As will be shown below, however, this device fails to address the viscous effects of blood flow through the needles, which contributes substantially to hemolysis in the resulting blood samples.

Thus, there is a need for an apparatus for drawing blood from a patient which substantially reduces the risk of hemolysis as blood is drawn into vacuum specimen tubes.

There is also a need for an apparatus for drawing blood which provides improved introduction into patients having poor peripheral access without the associated higher likelihood of hemolysis.

SUMMARY OF THE INVENTION

The present invention involves a syringe for collecting fluid samples, preferably blood samples from a patient, either percutaneously or from an indwelling catheter. Generally, the syringe comprises a substantially cylindrical body, having a closed distal end and an open proximal end. A plunger assembly is slidably inserted into the open proximal end. The plunger assembly includes a piston on its distal end which sealably engages the interior surface of the cylindrical body, thereby defining a fluid chamber between the piston face and the distal end of the cylindrical body.

The distal end of the cylindrical body includes a restricted distal opening therethrough, for providing influx and efflux of fluid between the syringe and a patient. Preferably, the distal opening extends distally through a hub on the distal end of the cylindrical body. A restriction is integrally fixed to the interior of the hub, defining a restricted opening in the distal opening. A conventional hypodermic needle is attached to the hub which allows the syringe to be percutaneously introduced into a patient's blood vessel. Alternatively, a catheter, already providing access into the patient, is connected to the hub.

In a preferred embodiment, a conduit communicates with the fluid chamber, providing a passage for withdrawing a fluid sample from the patient. Preferably, the conduit extends proximally from an opening in the piston face through the plunger assembly. The proximal end of the conduit is connected to a tube-holding device, generally a substantially cylindrical body adapted to receive vacuum specimen tubes therein.

The tube-holding device is preferably integral with the proximal end of the plunger assembly, although alternatively it may be a separate device beyond the proximal end of the plunger assembly. The tube-holding device has a closed distal end with an opening therethrough communicating with the conduit. A needle extends proximally from the opening and is generally covered by a conventional rubber seal. Thus, a conventional specimen tube may be inserted into the open proximal end of the device until the needle punctures the seal on the tube.

In another preferred embodiment, the conduit extends peripherally from the fluid chamber through the cylindrical body. Preferably, the conduit is located on the hub extending from the distal end of the cylindrical body, thereby preventing the conduit from being blocked when the plunger assembly is moved distally within the cylindrical body. The conduit extends beyond the cylindrical body and is connected to a tube-holding device, similar to that just described.

During use, the syringe of the present invention is generally provided with a hypodermic needle which is percutaneously introduced into a patient using conventional methods, or alternatively is connected to an indwelling catheter. Fluid is drawn into the fluid chamber by directing the plunger assembly distally. A vacuum specimen tube is then inserted into the tube-holding device until the seal of the tube engages the rubber seal around the needle and forces the needle to puncture both seals. The fluid chamber and the distal opening in the cylindrical body are thereby exposed to the low pressure of the interior of the specimen tube, forcing blood through the conduit and into the specimen tube.

The present invention substantially avoids the problems associated with conventional blood collection needles caused by the exposure of fluid, such as blood, to the uncontrollable initial low pressure of the specimen tube. The distal opening of the present invention is at least partially restricted in comparison to the conduit. This is achieved simply by providing a distal opening having a diameter substantially smaller than the lumen of the conduit, or by fixing a restriction, such as an annular obstruction, in the distal opening.

When the vacuum specimen tube is first inserted into the tube-holding device, the blood within the syringe is exposed to the fixed initial low pressure in the tube. Because of the smaller relative cross-section of the restricted opening, it has a greater viscous resistance to blood flow than the conduit. Thus, the restricted opening creates a pressure resistance, slowing blood flow through the conduit. To compensate, blood is preferentially drawn from the fluid chamber, decelerating the proximal movement of the plunger assembly. Thus, blood flow is controlled more precisely under the fixed pressure of the specimen tube using the present invention, thereby substantially reducing the likelihood of hemolysis within the sample obtained.

Furthermore, the syringe allows a smaller gauge hypodermic needle to be attached to the hub, without substantially increasing the risk of hemolysis. Because of the pressure drop across the restricted opening, the blood within the narrow needle is subjected to a lower pressure, thereby substantially reducing the strain on the blood and reducing the likelihood of hemolysis.

In another preferred embodiment, a syringe, similar to that previously described, is provided, however with a cannula which extends between the distal opening in the cylindrical body and the opening in the piston face. The cannula has an outer cross-section smaller than the opening in the distal end, thereby allowing fluid to pass around the cannula between the distal opening and the fluid chamber. The cannula is also supported at its distal end, preferably by a plurality of struts or ribs extending between the outer surface of the cannula and the inner walls of the distal opening.

The piston slidably engages the outer surface of the cannula, substantially sealing the conduit from the fluid chamber. Thus, fluid may communicate either between the distal opening in the cylindrical body and the fluid chamber, or between the distal opening and the conduit through the plunger assembly.

Preferably, a restriction is attached to the hub in the distal opening proximal of the distal end of the cannula. A first sample is drawn into the fluid chamber from the patient by directing the plunger assembly proximally. A vacuum specimen tube is then inserted into the tube holding device, drawing fluid from the patient through the cannula and into the tube. The restriction creates a substantial viscous resistance to flow through the restricted opening between the fluid chamber and the cannula, substantially eliminating the chance of fluid being drawn into the cannula from the fluid chamber rather than directly from the patient. Therefore, a fluid sample within the fluid chamber may be substantially isolated from a sample obtained through the cannula.

Thus, it is an object of the present invention to provide a syringe for taking blood samples from a patient for laboratory testing which substantially reduces the extent to which hemolysis occurs when blood is drawn from a patient using vacuum specimen tubes.

Another object is to provide a syringe which decelerates the distal and proximal movement of the plunger assembly, thereby slowing the influx and efflux of fluid through the syringe and substantially reducing hemolysis caused by uncontrolled blood flow.

It is a further object to provide a syringe providing improved introduction into a patient having poor peripheral access without substantially increased risk of hemolysis in the sample obtained.

It is also an object to provide a syringe allowing a first sample to be drawn which is substantially isolated from subsequent samples obtained for laboratory testing.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which.

DESCRIPTION OF THE PREFERRED EMBODIMENTS

Figure 1A:
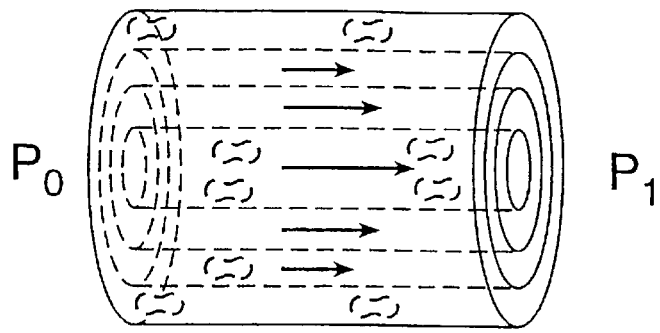
FIGS. 1A and 1B are schematic views, showing the flow of a viscous fluid through a cylindrical tube.

Before describing the preferred embodiments, a discussion of the general physics and fluid dynamics related to the present invention is presented. Pressure P is defined as a given force F distributed over a unit of area A, that is:

$$P=F/A. \tag{1}$$

After examining equation (1), it is apparent that the force F is directly proportional to the pressure P and inversely related to area A. Because force F is the product of mass m and acceleration a, from Newton's second law, pressure P can be defined using $$F=ma \tag{2}$$

as:

$$P=ma/A. \tag{3}$$

It should generally be appreciated that a syringe at rest has a pressure P within its barrel substantially equivalent to atmospheric pressure. The absolute value of the pressure P reflects the observed pressure of a syringe in use. Atmospheric pressure serves as a reference with the observed variable pressure dP within the syringe being above or below atmospheric pressure. With reference to a syringe in use, the mass involved is the sum of the masses of the piston and the plunger. Clearly, although the mass of a piston-plunger assembly varies with the size of the syringe used, for each individual syringe, the mass is fixed. Similarly, a syringe of a given size has a piston of a constant surface area. Thus equation (3) can be rewritten as follows:

$$dP = k_m da/k_A, \quad (4)$$

where $k_m$ is the constant mass of the piston-plunger assembly, $k_A$ is the constant surface area of the piston, and da is the changing acceleration associated with a variable pressure dP. Further, since a constant divided by a constant is simply another constant, equation (3) can be rewritten as:

$$dP = kda. \quad (5)$$

From equation (5), the observed pressure within any syringe in use is shown to be simply a function of the acceleration a of the piston-plunger assembly in a proximal or distal direction times some constant k. This acceleration is generally imparted by the technical skills of the health professional. Thus, the above principles show that a syringe of any volume, having a hypodermic needle attached to its distal end, will cause a fluid to experience an acceleration equal in magnitude and direction to the acceleration experienced by the piston-plunger assembly.

To appreciate the physics involved in the use of a conventional syringe, an understanding of fluid dynamics is essential. Newtonian fluids are governed by Bernoulli's equation:

$$P_a + \rho g y_a + 1/2 \rho v_a^2 = P_b + \rho g y_b + 1/2 \rho v_b^2 \quad (6)$$

which emphasizes that the pressure P plus the total mechanical energy per unit volume, $\rho gy + 1/2\rho v^2$, is constant everywhere in a flow tube. Because the blood flow in a syringe is essentially horizontal, the potential energy component, $\rho gy$, remains substantially unchanged. Therefore, equation (5) can be simplified to:

$$P_o + 1/2\rho v_o^2 = P_n + 1/2 \rho v_n^2. \quad (7)$$

In addition, the continuity equation for flow predicts that:

$$A_o v_o = A_n v_n, \quad (8)$$

or $$v_n = [A_o/A_n]v_o. \quad (9)$$

Using equation (9) for $v_n$, equation (6) can be rewritten as:

$$P_o - P_n = 1/2\rho v_o^2 (A_o^2/A_n^2 - 1). \quad (10)$$

Equation (10) above shows that the driving force on a Newtonian, non-viscous fluid is the pressure drop across the flow tube, $P_o - P_n$. From equation (9) above, the resultant velocity of a Newtonian fluid is a function of the cross-sectional area of the flow tube.

When considering blood flow, however, the laws governing non-Newtonian viscous fluids apply, rather than the Newtonian equations given above. By definition, viscosity $\eta$ is that inherent property of a fluid that resists motion, i.e. flow, and has units of mass, length, and time. According to Poiseuille's Law:

$$Q = \Delta P \pi R^4 / 8 \eta l. \quad (11)$$

Poiseuille's Law determines that the flow Q of a viscous fluid is directly proportional to a pressure drop $\Delta P$ and the fourth power of the radius of the flow tube. In the case of whole blood collection with a vacuum specimen tube, $\Delta P$ is constant and cannot otherwise be manipulated. Clearly then, an observed net flow of blood with viscosity $\eta$ into a vacuum tube is more a reflection of the surface area of the hypodermic needle having a radius r and a length l. Recognizing this, the viscous force that a pressure drop $\Delta P$ must overcome to observe a net flow of viscous blood is:

$$F = -\eta A dv/dr \quad (12)$$

where A is the surface area of the needle and dv/dr is the acceleration required. Therefore, the net driving force through a cylindrical tube having a radius r subjected to a pressure $\Delta P$ is $\Delta P \pi r^2$, which may be equated to the viscous force in equation (12) required to cause flow of the fluid, namely:

$$\Delta P \pi r^2 = \eta A dv/dr. \quad (13)$$

Because the pressure value $\Delta P$ is constant and fixed by the vacuum tube, equation (13) can be solved for velocity:

$$dv = \Delta P \pi r^2 dr/\eta A.$$

With the surface area of the needle being that of a cylinder, namely $2\pi r l$, this becomes:

$$dv = \Delta P r dr/2\eta l \quad (14)$$

Integrating both sides gives:

$$\int_v^0 dv = -\Delta P/2\eta l \int_r^R r dr, \quad (15)$$

$$v = \Delta P/4\eta l (R^2 - r^2).$$

Equation (15) shows that a maximum velocity $v_{max}$ occurs at r=0. In this equation, R is the radius of the diameter of the hypodermic needle and r is the radius of a thin cylindrical shell of viscous blood flowing through the hypodermic needle. Intuitively, it can be realized that laminar flow results in a long, narrow cylindrical tube, establishing a velocity gradient. This velocity gradient varies from zero along the inner wall of the hypodermic needle and increases to $v_{max}$, in the central portion of the blood flow. Maximum velocity of the blood occurs at r=0. Velocity approaches zero as r approaches R. Again, this variation in velocity is a consequence of laminar flow of a viscous fluid.

As a viscous fluid travels through a flow tube, it experiences a pressure drop due to the viscous losses through the tube. The viscosity of the fluid resists flow, with the greatest amount of resistance occurring along the inner wall of the flow tube where the velocity is essentially zero (v=0, r=R). The least amount of resistance occurs in the central portion of the fluid flow where the velocity is maximized (v=$v_{max}$, r=0). The integral v=0 to v=$v_{max}$ shows that the blood flow occurs in various thin cylinders of fluid at a given r, forming the basis for laminar flow.

When determining whether flow is laminar or turbulent, the following equation applies:

$$N_R = 2\rho v_{avg} R/\eta \quad (16)$$

where $N_R$ is Reynolds number. In a flow tube, experimentally it can be shown that:

$N_R < 2000$, flow is laminar $N_R>3000$, flow is turbulent $2000<N_R<3000$, flow may fluctuate between laminar and turbulent.

When considering the concepts of laminar and turbulent flow, each flow characteristic has an important role in a given fluid flow. For example, when a patient's blood pressure is measured, turbulent flow of blood is induced immediately after the constriction imposed on the artery. Energy is dissipated because of the turbulent flow and is lost as heat and sound, thereby allowing measurement of a patient's blood pressure using a sphygmomanometer and a stethoscope. Further, turbulent flow allows detection of heart murmurs and artereovenous malformations. Importantly, blood contains numerous cells and proteins which are randomly dispersed throughout the blood and are at equilibrium with each other. This randomness is key because the random organization causes minimal mechanical strain on the blood constituents.

Figure 1B:
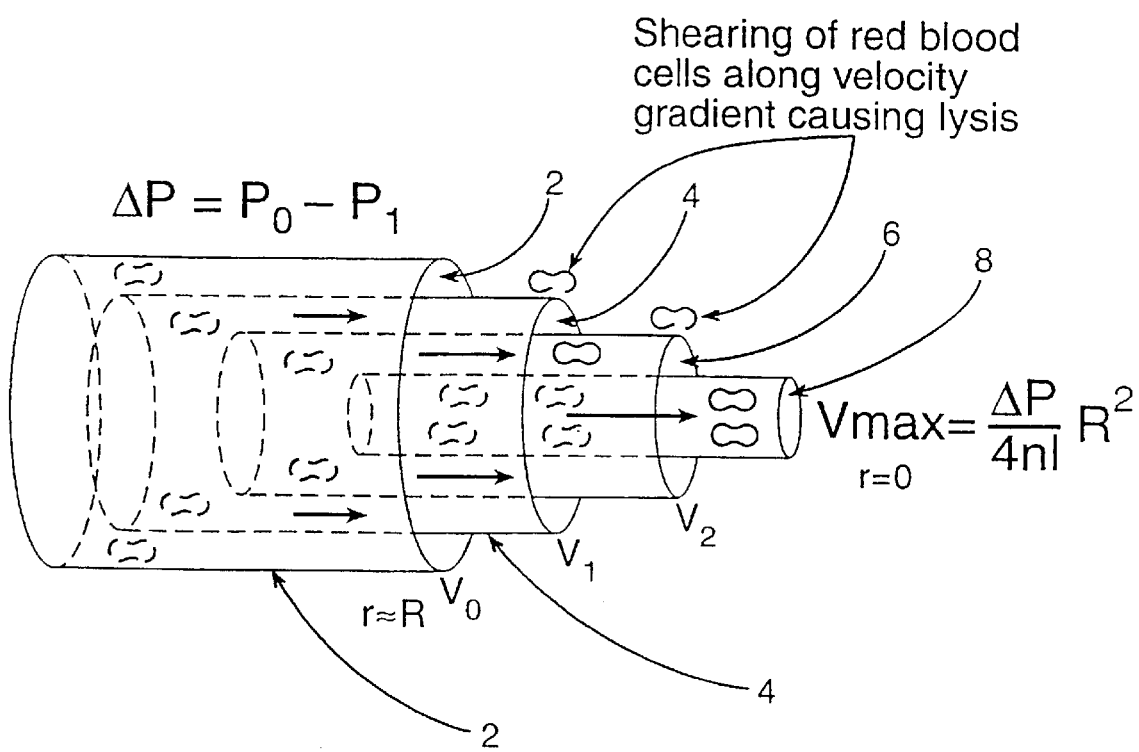

Laminar flow, which is illustrated in FIG. 1, requires a viscous fluid to absorb the energy imparted on it to cause a net fluid flow and maintain the highly organized lamina through the velocity gradient. This highly organized pattern of blood flow through a hypodermic needle causes a mechanical strain on all of the blood constituents, thereby contributing to hemolysis. For example, the outermost layer 2 generally does not move substantially because of the viscosity. The adjacent layer 4 will move in relation to the outermost layer 2, causing red blood cells in the lamina to shear as they move past one another. As the cells break down, potassium is released into the fluid, creating inaccurate specimens. In contrast, turbulent flow results in less efficient overall blood flow, but causes increased mixing of the lamina and the blood cells therein, reducing mechanical strain and consequently reducing hemolysis.

Returning to equation (16) above in light of this discussion, a lower Reynolds number results in laminar flow, increasing mechanical strain given a fixed $\Delta P$. Consequently, the blood constituents will experience more mechanical strain and therefore will be more likely to undergo hemolysis. Solving for the maximum velocity in equation (15) gives:

$$v_{max}=\Delta PR^2/4\eta l. \tag{17}$$

The average velocity of flow Q through a tube having a cross-sectional area, A, is:

$$v_{avg}=Q/A$$

Substituting for Q from Poiseuille's Law (equation (11)) and with the area, A, being that of a circle, $\pi R^2$, gives:

$$v_{avg}=(\Delta P\pi R^4/8\eta l)/A$$

$$v_{avg}=\Delta PR^2/8\eta l$$

Thus, comparing this to equation (17), the relationship between the average velocity in a fluid and the maximum velocity is:

$$v_{avg}=v_{max}/2.$$

These equations show that decreasing the needle radius by a factor of 2 will consequently decrease the average velocity of the blood by a factor of 4, and an overall decrease in the Reynolds number by a factor of 8. Such conditions represents a tremendous increase in the mechanical strain on the blood cells as they attempt to flow through a narrow needle.

Moss recognizes that a narrow needle lumen will decrease the velocity of the blood flowing through the needle and claims that this decreased velocity prevents hemolysis of the red blood cells. Moss fails to recognize that blood is a non-Newtonian fluid, and that the maximum velocity of the blood varies as the square of the radius and that this maximum velocity simply establishes a point from which a velocity gradient will occur. In other words, decreasing the radius of the flow tube simply increases the mechanical strain on the blood cells which is reflected by the decrease in the overall observed velocity, as more energy is absorbed by the viscous fluid in an effort to conform to the geometric constraints of individual lamina.

Additionally, an increase in the flow resistance is observed given that the pressure drop across the flow tube is constant, as is shown by:

$$R_f=8\eta l/\pi R^4 \tag{18}$$

where $R_f$ is obtained from equation (11) and is defined as:

$$R_f=\Delta P/Q. \tag{19}$$

Equation (18) shows that the resistance to flow $R_f$ varies as the inverse of the fourth power of the radius. Clearly, for every small reduction in R, there is a significant reduction in the flow Q, and a significant increase in resistance $R_f$. The velocity of the blood only examines the individual lamina of fluid within a flow tube. Changing the radius of the flow tube also affects the average velocity within the flow tube as described above. Thus, a change in radius will have a greater effect on Reynolds number. The lower Reynolds Number will create a more constrained environment in which laminar flow must occur and will cause hemolysis, that is, the blood cells will shear and release potassium from their cytoplasm.

Equation (17) shows that $v_{max}$ is directly proportional to $\Delta P$ and the square of the radius of the flow tube. As the flow environment becomes more constrained as a result of a decrease in R, the average velocity is decreased by a factor of 4 as described above. On the other hand, for every change in the pressure drop $\Delta P$, there is a linear drop in the maximum velocity. Therefore, the flow environment will be less dynamically constrained according to Reynolds number. Because fluid flow will be laminar as long as the Reynolds number is less than 2000, the slope of the velocity gradient imparts the mechanical strain on the red blood cells. A decreasing radius of the flow tube will increase the slope of the velocity gradient given a fixed pressure drop, i.e., the vacuum specimen tube.

Figure 2:
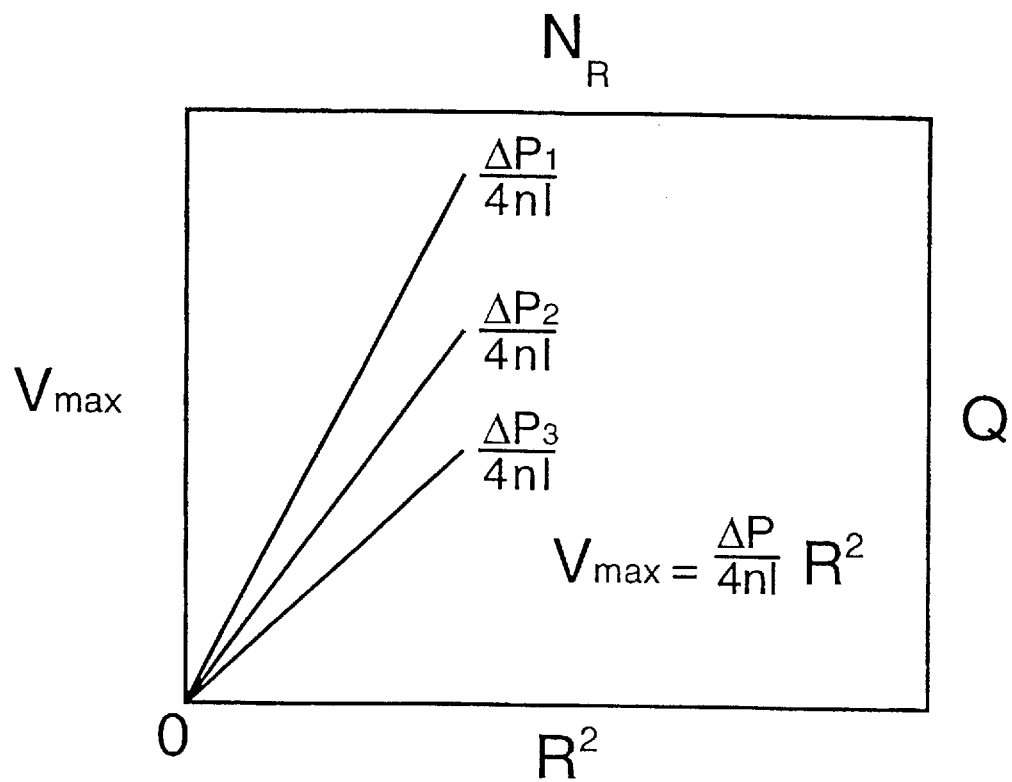
FIG. 2 is a graph showing the effect of increasing the pressure applied to a flow tube on the velocity gradient of a viscous fluid flowing therethrough.
Figure 3:
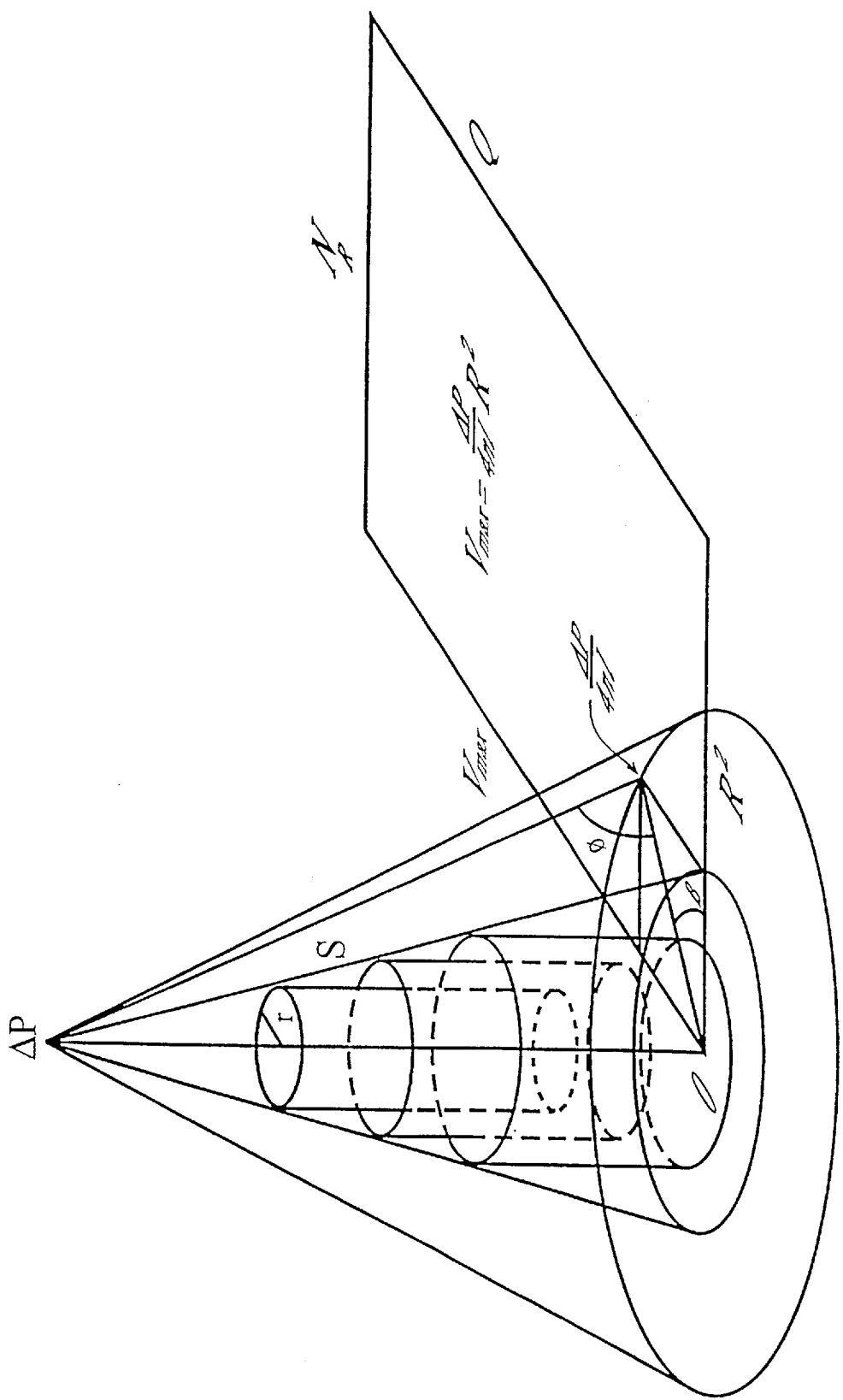
FIG. 3 is a chart showing the effect of decreasing the radius of a flow tube on the velocity gradient of a viscous fluid flowing therethrough.

Referring once again to equation (17), the maximum velocity can be shown to fit the equation of a line:

$$y=mx+b, \tag{20}$$

where m is the slope and b is the y intercept. In the present case, $y=v_{max}$, $m=\Delta P/4\eta l$, $x=(R^2-r^2)$, and $b=0$, recalling that $r^2=0$ at $v_{max}$. Given this equation, $v_{max}$ may be plotted as a function of R. Referring to FIGS. 2 and 3, it should be appreciated that the mechanical strain on the red blood cells increases as the radius R of the flow tube decreases, i.e. an increasing slope with a decreasing radius. A decrease in the pressure drop $\Delta P$ decreases the slope of the velocity gradient, i.e., resulting in less mechanical strain on the red blood cells.

Moss describes a double needle for vena puncture, the front needle ranging in size from 23 to 29 gauge and the rear needle ranging from 12 to 16 gauge. Moss describes the front smaller needle as a flow restriction, thereby decreasing the velocity of the blood as it flows through the front needle.

However, if low velocity blood flow is to be maintained as the blood enters a vacuum tube, the restricted needle would have to be continuous throughout its length. Moss recognized that if the small gauge needle were continuous, it would be unable to penetrate the rubber stop of the vacuum specimen tube, and he therefore increased the size of the rear needle.

Moss does not recognize that a decreasing radius increases the slope of the velocity gradient. Referring to FIG. 3, the slope S represents the velocity gradient across a flow tube having a radius R and subject to a pressure $\Delta P$. Thus, because $\Delta P/4\eta l$ is a constant fixed by the vacuum tube and the needle, as R is reduced, the slope S, that is the velocity gradient, is increased. Further, if $\Delta P$ is increased, while R remains constant, the slope is again increased (not shown). Moss' device increases the velocity gradient in the front needle because of its smaller radius, thereby increasing the mechanical strain on the red blood cells. Thus, Moss simply describes a double needle having a small radius front needle for penetrating small veins that actually increases hemolysis in the blood rather than preventing it as intended.

Clearly, the Moss needle does not follow the physics which govern the dynamics of a non-Newtonian fluid. Further, based upon the mechanics described, Moss cannot even follow the concepts of the continuity equation for a Newtonian fluid, i.e., small radius high velocity, large radius low velocity, as presented in equation (8) above.

Given the principles expressed above, the issue of mechanical strain as a consequence of a laminar velocity gradient may be addressed by increasing the radius of the flow tube or decreasing the pressure drop across the flow tube. Clearly, when attempting to collect blood from a patient with poor peripheral access, a small gauge needle is required, i.e., a small radius. Because this small radius increases the mechanical strain on the blood cells, it must be counterbalanced. Furthermore, the vacuum specimen tube provides a fixed pressure drop across the blood collection needle and cannot otherwise be manipulated. Equation (3) above demonstrated that the differential pressure dP is directly proportional to the differential acceleration da of the piston-plunger assembly having a constant mass k.

Given these principles, the mechanical strain caused by the laminar velocity gradient may be effectively addressed in a number of ways. Assuming the small gauge needle is required and its diameter cannot be increased, the effective $\Delta P$ across the flow tube must be decreased to counteract the strain. Given the physical configuration of a conventional syringe, the pressure drop can be reduced by decelerating the proximal movement of the piston-plunger assembly. Preferably this is achieved by restricting the distal opening in the cylindrical body of the syringe. Alternatively, the overall length of the cylindrical body may be decreased, the frictional resistance between the piston and the inner wall of the cylindrical body may be increased, the surface area of the piston may be decreased, and/or the mass of the piston-plunger assembly may be decreased. Further deceleration may be achieved if necessary by pulling more slowly on the piston-plunger assembly when drawing blood.

To summarize, when a vacuum specimen tube is inserted into prior art devices, such as Moss' device, the pressure from the initial vacuum in the specimen tube is exerted onto the fluid in the rear needle. Blood travels proximally through the rear needle into the specimen tube, applying a similar pressure on blood within the front needle. However, because the front needle has a smaller cross-section, the pressure imposes a greater strain on the fluid traveling therethrough. This increased strain on the blood trying to flow through the narrow needle increases the likelihood of hemolysis of the blood, providing less desirable blood samples.

In contrast, the present invention includes a reservoir, the fluid chamber, from which blood is drawn into the conduit and subsequently into the specimen tube. This reduces the amount of blood that must pass through the distal opening, reducing the strain and hemolysis that may occur therein. This preferential flow from the fluid chamber also decelerates the proximal movement of the plunger assembly. Furthermore, the restriction in the distal opening creates a pressure resistance, thereby reducing the pressure to which blood in the hypodermic needle is exposed. Thus, a smaller gauge needle may be connected to the hub without substantially risking increased strain and hemolysis of the blood flowing therethrough.

Figure 4:
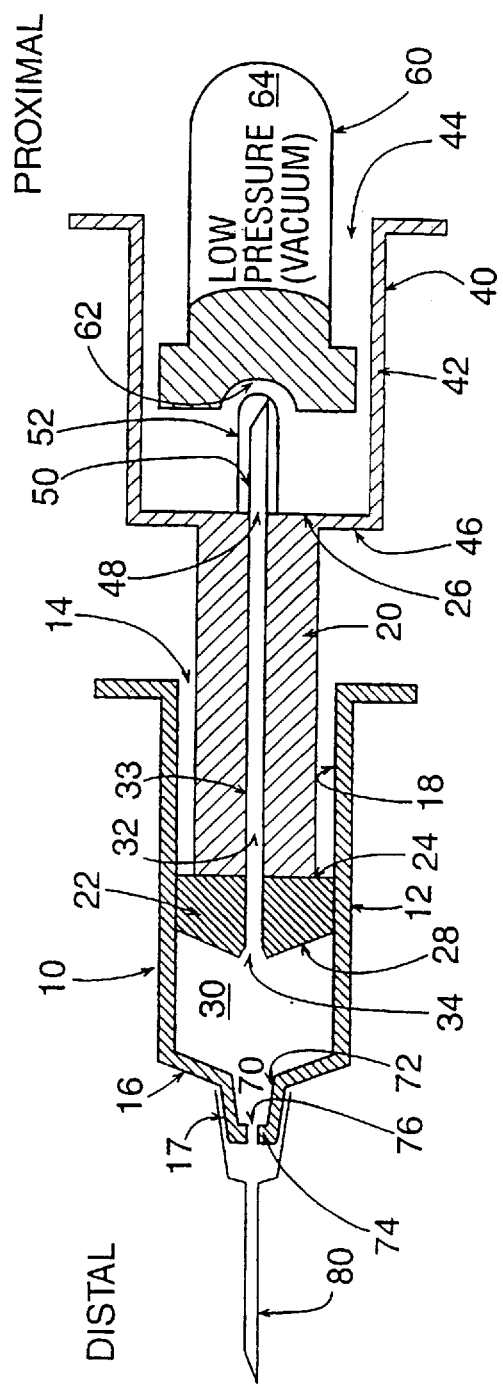
FIG. 4 is a cross-section of a preferred embodiment of the present invention, including a hypodermic needle and a tube-holding device.

Turning now to FIG. 4, a preferred embodiment of the present invention is shown, namely a syringe 10. The syringe 10 includes a substantially cylindrical body 12, having an open proximal end 14 and a closed distal end 16. A plunger assembly 20, an elongate member having a distal end 24 and a proximal end 26, is slidably inserted into the proximal end 14 of the cylindrical body 12. The plunger assembly 20 includes a piston 22 attached to the distal end 24 of the plunger assembly 20. The piston 22 sealably engages the interior wall 18 of the cylindrical body 12, thereby defining a fluid chamber 30 between the piston face 28 and the distal end 16 of the cylindrical body 12.

A conduit 32, defining a lumen 33, extends proximally from an opening 34 in the piston face 28 through the plunger assembly 20, thereby providing passage between the fluid chamber 30 and the proximal end 26 of the plunger assembly 20 through which blood samples may be obtained.

Attached to the proximal end 26 of the plunger assembly 20 is a tube-holding device 40. The tube-holding device 40 comprises a substantially cylindrical body 42 having on open proximal end 44 and a closed distal end 46. An opening 48 in the distal end 46 communicates with the conduit 32. A needle 50 is attached to the distal end 46 concentric with the opening 48 and is covered by a conventional rubber seal 52. A conventional vacuum specimen tube 60 is shown being inserted into the proximal end 44.

A hub 17 is attached to and extends distally from the distal end 16 of the cylindrical body 12, the hub 17 having an opening 70 extending distally therethrough. A conventional hypodermic needle 80 is attached to the hub 17, although alternatively a catheter may be attached thereto. Attached to the interior wall 72 of the hub 17 is a restriction 74 defining a restricted opening 76 which substantially restricts the distal opening 70. The restriction 72 is preferably an annular obstruction integrally fixed to the interior wall 72 of the hub 17, thereby defining a restricted opening 76 having a diameter substantially less than the distal opening 70 and preferably substantially less than the lumen 33 of the conduit 32. Although the restriction 74 is shown substantially covering the entire interior wall 72, other obstructions such a plurality of struts or even a single protrusion which substantially restricts the cross-section of the distal opening 70 may be provided.

The materials of the cylindrical body 12, the plunger assembly 20, and the tube-holding device 40 are substantially conventional and should be familiar to those reasonably skilled in the art. The piston 22 generally comprises a flexible substantially resilient material, sealably engaging the interior wall 18 of the cylindrical body 12 in a substantially liquid tight manner, and allowing the plunger assembly 20 to be directed proximally and distally by overcoming the relatively slight frictional resistance created by the engagement between the piston 22 and the interior wall 18.

Generally, the syringe 10 is percutaneously introduced into a patient using conventional methods, although alternatively it may be connected to an indwelling catheter. The plunger assembly 20 is directed proximally, drawing blood through the hypodermic needle 80 and the distal opening 70 into the fluid chamber 30. A conventional vacuum specimen tube 60 is then inserted into the proximal end 44 of the tube-holding device 40 until the seal 62 on the tube 60 is punctured by the needle 50. Thus, a continuous passage is created between the hypodermic needle 80, the distal opening 70, the fluid chamber 30, the conduit 32, the needle 52, and the interior 64 of the specimen tube 60.

Because the interior 64 of the specimen tube 60 has a fixed initial low pressure, it imposes a sudden proximal pressure and force on the conduit when it is inserted into the tube-holding device 40, drawing blood into the specimen tube 60 from the conduit 32. Because of the flow induced by the vacuum, the low pressure is translated to the fluid chamber 30, and consequently to the distal opening 70. However, because the restriction 74 in the distal opening 70 creates a relatively high viscous resistance to flow, a substantial pressure drop is created across the restricted opening 76, substantially reducing the pressure on blood flowing into the fluid chamber 30 from the hypodermic needle 80.

Because the frictional resistance between the piston 22 and the interior wall 18 of the cylindrical body 12 is substantially less than the viscous resistance through the restricted opening 76, the pressure from the vacuum tube 60 preferentially draws fluid from the fluid chamber 30. This creates a pressure against the piston face 28 which resists proximal movement of the plunger assembly 22, or possibly even draws the plunger assembly 22 distally as fluid is drawn from the fluid chamber 30 into the conduit 32. As the specimen tube 60 is filled, the pressure decreases, allowing additional fluid to slowly enter through the distal opening 70 without causing strain on the fluid as it is drawn through the hypodermic needle 80. If additional fluid needs to be drawn into the fluid chamber 30 from the patient, the operator of the device may overcome the deceleration of the plunger assembly and draw the plunger assembly proximally. Thus, health professionals may more directly control the effects of the low pressure from the initial vacuum of the specimen tube, substantially minimizing the likelihood of hemolysis occurring when the syringe is used to obtain blood samples from a patient.

Figure 5:
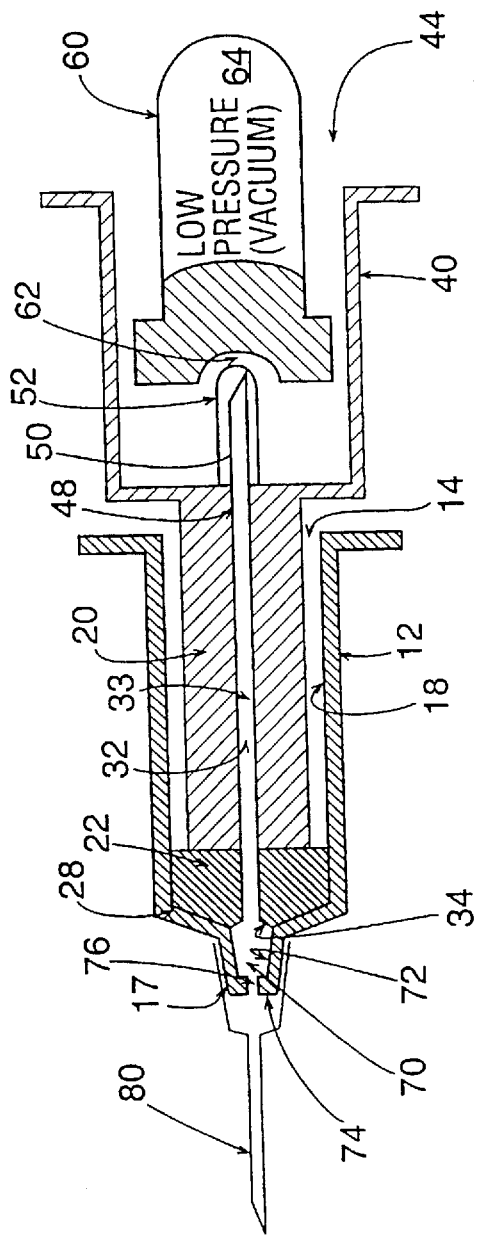
FIG. 5 is a cross-section of an alternative embodiment, for use with large hypodermic needles.

Alternatively, as shown in FIG. 5, the syringe 10 is used to obtain samples without first drawing fluid into the fluid chamber 30. In this embodiment, the plunger assembly 20 is held in its distal position, whereby the opening 34 in the piston face 28 communicates substantially directly with the distal opening 70. This alternative, however, is generally only used when a relatively large hypodermic needle 80 is used to gain access to a relatively large blood vessel. In such cases, the viscous effects of blood flow through the needle 80 and the distal opening 70 are minimized, and poor peripheral access into a patient's blood vessels is not a substantial concern.

Figure 6:
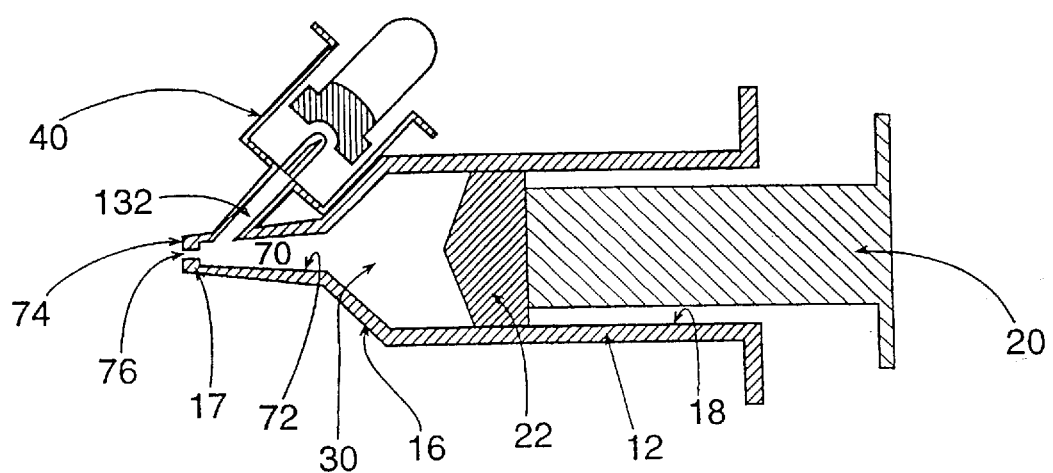
FIG. 6 is a cross-section of another preferred embodiment, having the conduit and tube-holding device located peripherally from the syringe body but communicating with the fluid chamber.

Referring now to FIG. 6, another preferred embodiment is shown, including a cylindrical body 12, and a plunger assembly 20 similar to that previously described. Rather than having a conduit extending proximally from the piston face to a tube-holding device, however, a conduit 132 is connected peripherally to the cylindrical body 12, preferably to the hub 17 extending distally from the cylindrical body 12. The hub 17 has a distal opening 70 extending therethrough communicating with the fluid chamber 30, and has a restriction 72 integrally attached to its interior wall 72. Preferably, the conduit 132 is attached to the hub 17 proximal of the restriction 74, allowing the conduit 132 to substantially communicate directly with the fluid chamber 30. The restriction 72 defines a restricted opening 76, providing access to the patient.

The conduit 132 may comprise a tube, such as conventional medical tubing, detachably connected to a nipple (not shown) projecting peripherally from the hub 17, or alternatively it may be integrally formed into the cylindrical body 12. A tube-holding device 40, similar to that previously described, is attached to the conduit 132, allowing a fluid sample to be drawn into a specimen tube 60 inserted therein.

Generally, fluid is initially drawn into the fluid chamber 30 by directing the plunger assembly 20 proximally. A vacuum tube 60 is inserted into the tube-holding device 40, causing fluid to be drawn through the conduit 132 and into the tube 60. Because the restriction 74 imposes a viscous resistance to flow through the restricted opening 76, fluid is preferentially drawn into the conduit 132 from the fluid chamber 30, substantially reducing strain on blood flowing through the distal opening 70, and decelerating proximal movement of the plunger assembly 20.

Figure 7:
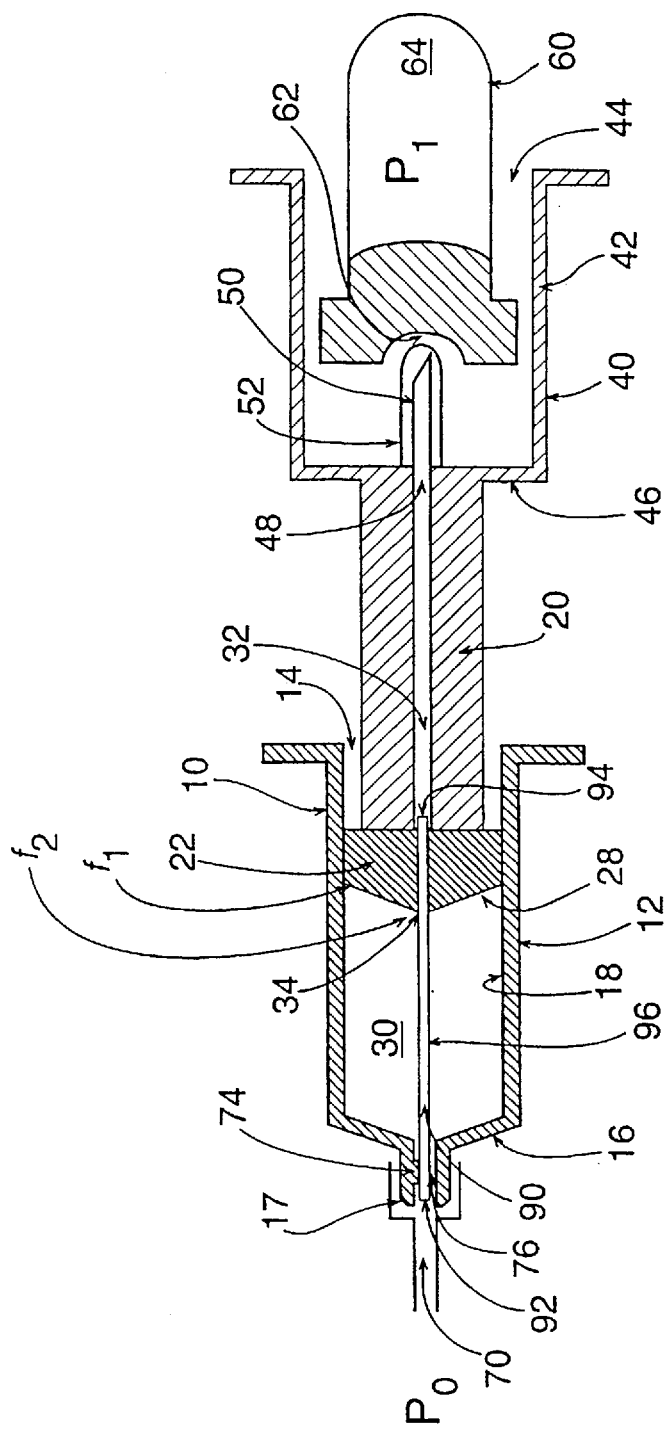
FIG. 7 is a cross-section of another preferred embodiment, having a cannula isolating the fluid chamber from the conduit in the plunger assembly.

Turning now to FIG. 7, another preferred embodiment of the present invention is shown, namely a syringe 10, similar to those previously described, comprising a substantially cylindrical body 12, a plunger assembly 20, and a tube-holding device 40. In addition, the syringe 10 includes an inner cannula 90, having a distal end 92 and a proximal end 94. The distal end 92 extends into the hub 17 on the distal end 16 of the cylindrical body 12, where it is preferably fixed to the hub with struts or ribs (not shown). A restriction 74 is integrally fixed within the hub 17 preferably proximal of the distal end 92 of the cannula 90, thereby defining a restricted opening 76 between the outer surface 96 of the cannula and the restriction 74. Alternatively, the struts fixing the cannula 90 to the hub 17 may provide sufficient restriction for the purposes of the present invention.

The proximal end 94 of the cannula 90 communicates with the conduit 32 passing through the plunger assembly 20. Preferably, the cannula 90 extends into the opening 34 in the piston face 28, and the piston 22 slidably engages the outer surface 96 of the cannula 90, thereby sealably isolating the fluid chamber 30 from the conduit 32.

The syringe 10 is percutaneously introduced into a patient, or is attached to an indwelling catheter (not shown). The plunger assembly 20 is directed proximally, drawing fluid through the restricted opening 76 into the fluid chamber 70. Once a desired first fluid sample is contained within the fluid chamber 30, a vacuum specimen tube 60 is inserted into the tube-holding device 40. The vacuum within the interior 64 of the specimen tube 60 draws fluid from the patient through the distal end 92 of the cannula 90, through the conduit 32 and into the tube 60.

Because the restriction 76 obstructs the distal opening 70, the viscous resistance to flow from the fluid chamber 30 through the restricted opening 76 is substantially higher than the flow directly from the patient through the needle 80. Thus, the vacuum tube preferentially draws a fluid sample directly from the patient, rather than from the fluid chamber 30. Thus, the first sample contained in the fluid chamber 30 is substantially isolated from a subsequent sample obtained in the specimen tube 60.

Figure 8:
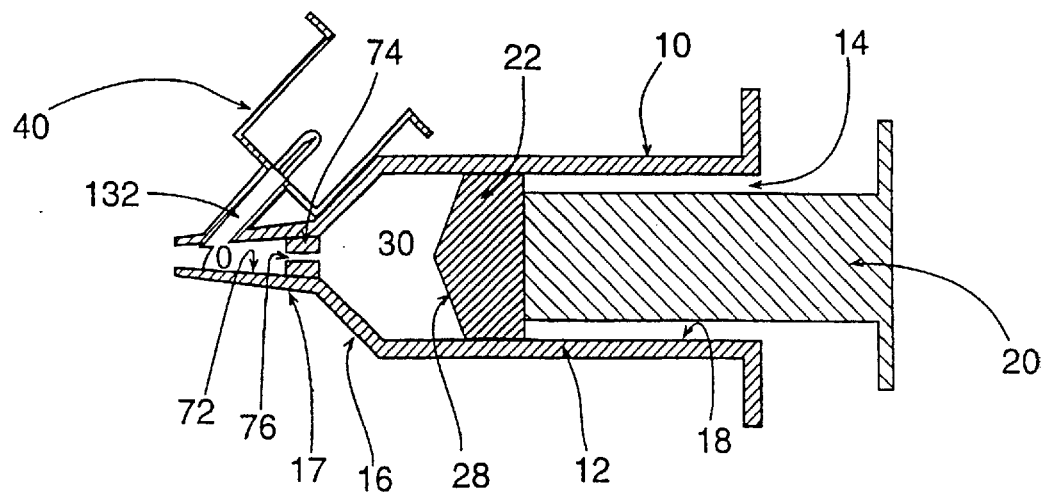
FIG. 8 is a cross-section of another preferred embodiment, having the conduit and tube-holding device located peripherally from the syringe body, but separated from the fluid chamber by a restricted opening.

In another preferred embodiment, shown in FIG. 8, the syringe 10 comprises a cylindrical body 12, a plunger assembly 20, and a tube-holding device 40. A hub 17 extends distally from the closed distal end 16 of the cylindrical body 12 and includes a distal opening 70 extending therethrough.

A restriction 74 is integrally attached to the interior wall 72 of the hub 17, defining a restricted opening 76 between the distal opening 70 and the fluid chamber 30. A conduit 132 is attached to the hub 17, preferably distal of the restriction 74, and communicates with the tube-holding device 40.

Preferably, the syringe 10 is attached to an indwelling catheter which has been introduced into a patient (not shown). The plunger assembly 20 is directed proximally, drawing fluid from the catheter (not shown) into the fluid chamber 30. A vacuum specimen tube (not shown) is then inserted into the tube-holding device 40, causing fluid to flow through the conduit 132 and into the tube (not shown).

Because the restriction 74 imposes a substantial viscous resistance to flow through the restricted opening 76, fluid is preferentially drawn through the conduit 132 directly from the patient, and the fluid sample contained within the fluid chamber 30 is substantially isolated from the specimen tube sample.

The present syringe allows a first sample fluid, e.g. a fluid medication being delivered into a patient's blood vessel through the catheter, to be withdrawn from the catheter into the fluid chamber 30 of the syringe 10. This draws blood from the patient's blood vessel into the catheter towards the syringe 10. When a specimen tube is then inserted into the tube-holding device, the low pressure draws blood directly from the catheter that is substantially free of any medication that may contaminate tests run on the sample obtained. Once a desired number of samples is obtained, the plunger assembly 20 is directed distally, reintroducing the first sample back into the catheter, for example allowing ongoing delivery of the medication into the patient.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A medical syringe for obtaining a fluid sample from a patient comprising
   a cylindrical body having an interior wall, an open proximal end, and a closed distal end, said distal end having a distal opening therethrough;
   a plunger assembly slidably inserted into said proximal end, said plunger assembly sealably engaging said interior wall, thereby defining a fluid chamber between a distal end of said plunger assembly and said distal end of said cylindrical body;
   a conduit extending from said fluid chamber, said conduit being adapted to receive a sample fluid therethrough; and
   a restriction fixed in said distal opening, said restriction providing a substantial viscous resistance to flow through said distal opening.

2. The medical syringe of claim 1 wherein said restriction in said distal opening comprises a substantially annular obstruction defining a restricted opening therethrough, thereby providing a viscous resistance to flow through said distal opening that is substantially greater than a frictional resistance of said plunger assembly to proximal or distal movement.

3. The medical syringe of claim 2 further comprising a vacuum specimen tube detachably connected to said conduit, said specimen tube having a fixed initial low pressure, thereby drawing a fluid sample through said conduit, said fluid sample being preferentially drawn from said fluid chamber due to said viscous resistance of said restriction in said distal opening, thereby substantially minimizing hemolysis in said fluid sample caused by uncontrolled flow of fluid through said distal opening.

4. The medical syringe of claim 1 wherein said conduit extends proximally through said plunger assembly.

5. The medical syringe of claim 4 further comprising a cannula extending proximally from said distal opening to said conduit.

6. The medical syringe of claim 5 further comprising a vacuum specimen tube detachably connected to said conduit, said specimen tube drawing a fluid sample through said conduit, said fluid sample being preferentially drawn from said distal opening rather than from said fluid chamber due to said viscous resistance of said restriction, thereby substantially isolating said fluid sample from a fluid sample within said fluid chamber.

7. The medical syringe of claim 1 wherein said conduit extends substantially peripherally from said cylindrical body.

8. The medical syringe of claim 1 further comprising a tube-holding device communicating with said conduit, said tube-holding device being adapted to receive a vacuum specimen tube therein.

9. The medical syringe of claim 8 further comprising a vacuum specimen tube having a fixed initial low pressure, said specimen tube being detachably inserted into said tube-holding device, said low pressure communicating with said fluid chamber, thereby preferentially drawing a fluid sample from said fluid chamber and decelerating the proximal movement of said plunger assembly.

10. The medical syringe of claim 1 further comprising
    a hub integrally attached to said distal end of said cylindrical body, said distal opening extending distally through said hub, said restriction being integrally fixed to an interior wall of said hub; and
    a relatively small gauge hypodermic needle attached to said hub, wherein said restriction substantially reduces the force imposed upon a fluid flowing through said hypodermic needle, thereby substantially reducing the likelihood of hemolysis in said fluid.

11. A medical syringe for obtaining a plurality of blood samples from a patient comprising
    a cylindrical body having an open proximal end, a closed distal end, and an interior wall, said distal end having a distal opening, said distal opening having a restriction therein to define a first viscous resistance to a fluid flow therethrough;
    a plunger slidably inserted into said proximal end of said cylindrical body, said plunger having a proximal end and a distal end;
    a piston attached to said distal end of said plunger, said piston sealably engaging said interior wall, thereby defining a fluid chamber between a piston face of said piston and said distal end of said cylindrical body;
    a tube-holding device on said proximal end of said plunger, said tube-holding device being adapted to receive a vacuum specimen tube therein; and
    a conduit extending proximally from said piston face through said plunger to said tube-holding device, said conduit defining a second viscous resistance to a fluid flow therethrough
    wherein said restricted opening in said distal end has a size with respect to said conduit such that said second viscous resistance is substantially less than said first viscous resistance.

12. The medical syringe of claim 11 further comprising a vacuum specimen tube detachably inserted into said tube-holding device, said specimen tube having a fixed initial low pressure which communicates through said conduit and preferentially draws a fluid sample from said fluid chamber, thereby substantially minimizing hemolysis in the sample.

13. A method for withdrawing a plurality of fluid samples from a patient comprising the steps of
providing a syringe having a restricted distal opening, a plunger assembly, a fluid chamber, and a conduit extending from the fluid chamber to a tube-holding device;
drawing the plunger assembly proximally, thereby introducing fluid into the fluid chamber through the distal opening; and
inserting a vacuum specimen tube into the tube-holding device, thereby drawing a fluid sample into the specimen tube preferentially from the fluid chamber, and thereby decelerating proximal movement of the plunger assembly.

14. The method of claim 13 comprising the additional step of drawing the plunger proximally after said inserting a vacuum specimen tube step, thereby drawing additional fluid into the fluid chamber through the restricted distal opening.

15. A medical syringe for obtaining a fluid sample from a patient, said medical syringe comprising:
a cylindrical body having an interior wall, an open proximal end, and a closed distal end, said distal end having a distal opening therethrough;
a plunger assembly slidably inserted into said proximal end and sealably engaging said interior wall, thereby defining a fluid chamber between a distal end of said plunger assembly and said distal end of said cylindrical body;
a conduit extending substantially proximally from said fluid chamber through said plunger assembly, said conduit being adapted to receive a sample fluid therethrough from said fluid chamber; and
a tube-holding device integral with said proximal end of said plunger assembly, said tube-holding device being adapted to receive a vacuum specimen tube therein.

16. The medical syringe of claim 15, further comprising a needle permanently attached to a proximal end of said plunger assembly and in communication with said conduit, said needle being adapted to penetrate the seal on a vacuum specimen tube.

17. The medical syringe of claim 16, further comprising a rubber seal attached to said proximal end of said plunger assembly, and substantially covering said needle.

18. The medical syringe of claim 15, further comprising:
a hub integrally attached to said distal end of said cylindrical body, said distal opening extending distally through said hub; and
a relatively small gauge hypodermic needle attached to said hub.

19. A medical syringe for obtaining a fluid sample from a patient, said medical syringe, comprising:
a cylindrical body having an interior wall, an open proximal end, and a closed distal end, said distal end having a distal opening therethrough;
a plunger assembly slidably inserted into said proximal end and sealably engaging said interior wall, thereby defining a fluid chamber between a distal end of said plunger assembly and said distal end of said cylindrical body;
a conduit extending substantially proximally from said fluid chamber through said plunger assembly, said conduit being adapted to receive a sample fluid therethrough from said fluid chamber;
a tube-holding device integral with said proximal end of said plunger assembly, said tube-holding device being adapted to receive a vacuum specimen tube therein; and
a restriction fixed in said distal opening providing a substantial viscous resistance to flow through said distal opening.

20. A method of withdrawing a plurality of blood samples from a patient, comprising the steps of:
providing a syringe having a restricted distal opening, a plunger assembly, a tube-holding device integral with the plunger assembly, and a conduit extending from a fluid chamber in the syringe through the plunger assembly to the tube-holding device;
percutaneously connecting the restricted distal opening with a blood vessel of a patient;
drawing the plunger assembly proximally, thereby introducing blood into the fluid chamber from the blood vessel through the restricted distal opening; and
inserting a vacuum specimen tube into the tube-holding device, thereby preferentially drawing a blood sample into the specimen tube through the conduit from the fluid chamber.

21. A method of withdrawing a plurality of blood samples from a patient, comprising the steps of:
providing a syringe having a restricted distal opening, a plunger assembly, a tube-holding device integral with the plunger assembly, and a conduit extending from a fluid chamber in the syringe through the plunger assembly to the tube-holding device;
percutaneously connecting the restricted distal opening with a blood vessel of a patient;
drawing the plunger assembly proximally, thereby introducing blood into the fluid chamber from the blood vessel through the restricted distal opening; and
inserting a vacuum specimen tube into the tube-holding device, thereby preferentially drawing a blood sample into the specimen tube through the conduit from the fluid chamber;
wherein the restricted distal opening defines a viscous resistance to flow therethrough, the viscous resistance to flow being substantially greater than a frictional resistance of the plunger assembly to distal and proximal movement;
wherein said step of inserting a vacuum specimen tube into the tube-holding device includes the step of penetrating a seal on the vacuum specimen tube with a needle in the tube-holding device, thereby imposing a sudden negative pressure on the fluid within the fluid chamber; and
wherein the viscous resistance of the restricted distal opening slows flow of blood through the distal opening when the sudden negative pressure is imposed to facilitate preferentially drawing blood from the fluid chamber and to decelerate proximal movement of the plunger assembly, thereby minimizing hemolysis in the blood sample received in the vacuum specimen tube.

* * * * *